US009592246B2

(12) United States Patent
Salman et al.

(10) Patent No.: US 9,592,246 B2
(45) Date of Patent: Mar. 14, 2017

(54) TETRACYCLINE TOPICAL FORMULATIONS, PREPARATION AND USES THEREOF

(71) Applicant: Hovione International Ltd., Wanchai (HK)

(72) Inventors: Mohammad Salman, Princeton, NJ (US); Arturo Angel, Santa Rosa, CA (US); Vijaya Swaminathan, San Francisco, CA (US)

(73) Assignee: Hovione International Ltd., Hong Kong (HK)

( * ) Notice: Subject to any disclaimer, the term of this patent is extended or adjusted under 35 U.S.C. 154(b) by 271 days.

(21) Appl. No.: 14/074,868

(22) Filed: Nov. 8, 2013

(65) Prior Publication Data

US 2014/0147504 A1 May 29, 2014

(30) Foreign Application Priority Data

Nov. 27, 2012 (PT) .......................... 106679

(51) Int. Cl.
| | | |
|---|---|---|
| A61K 31/65 | (2006.01) | |
| A61K 9/10 | (2006.01) | |
| A61K 9/00 | (2006.01) | |
| A61K 31/192 | (2006.01) | |
| A61K 31/203 | (2006.01) | |
| A61K 31/4436 | (2006.01) | |
| A61K 47/06 | (2006.01) | |

(52) U.S. Cl.
CPC ............ *A61K 31/65* (2013.01); *A61K 9/0014* (2013.01); *A61K 9/0048* (2013.01); *A61K 9/10* (2013.01); *A61K 31/192* (2013.01); *A61K 31/203* (2013.01); *A61K 31/4436* (2013.01); *A61K 47/06* (2013.01)

(58) Field of Classification Search
None
See application file for complete search history.

(56) References Cited

U.S. PATENT DOCUMENTS

| | | | |
|---|---|---|---|
| 4,119,717 A | 10/1978 | von Daehne et al. | |
| 4,505,896 A | 3/1985 | Bernstein | |
| 5,122,519 A | 6/1992 | Ritter | |
| 5,747,058 A | 5/1998 | Tipton et al. | |
| 5,834,008 A | 11/1998 | Greenspan et al. | |
| 5,874,479 A | 2/1999 | Martin | |
| 5,905,092 A | 5/1999 | Osborne et al. | |
| 6,113,921 A | 9/2000 | Friedman et al. | |
| 6,667,045 B2 | 12/2003 | Dahle | |
| 6,893,665 B2 | 5/2005 | Lawter et al. | |
| 6,911,211 B2 | 6/2005 | Eini et al. | |
| 6,967,023 B1 | 11/2005 | Eini et al. | |
| 6,994,863 B2 | 2/2006 | Eini et al. | |
| 7,241,746 B2 | 7/2007 | Wingrove et al. | |
| 7,531,164 B2 | 5/2009 | Daaka et al. | |
| 7,655,676 B2 | 2/2010 | Malabarba et al. | |
| 7,682,623 B2 | 3/2010 | Eini et al. | |
| 7,700,076 B2 | 4/2010 | Tamarkin et al. | |
| 7,704,518 B2 | 4/2010 | Tamarkin et al. | |
| 7,820,145 B2 | 10/2010 | Tamarkin et al. | |
| 7,854,938 B2 | 12/2010 | Ueda et al. | |
| 8,008,345 B2 | 8/2011 | West et al. | |
| 8,039,020 B2 | 10/2011 | Lapidot et al. | |
| 8,114,385 B2 | 2/2012 | Tamarkin et al. | |
| 8,343,945 B2 | 1/2013 | Tamarkin et al. | |
| 8,362,091 B2 | 1/2013 | Tamarkin et al. | |
| 8,435,498 B2 | 5/2013 | Tamarkin et al. | |
| 8,486,374 B2 | 7/2013 | Tamarkin et al. | |
| 8,486,375 B2 | 7/2013 | Tamarkin et al. | |
| 8,512,718 B2 | 8/2013 | Eini et al. | |
| 8,518,376 B2 | 8/2013 | Tamarkin et al. | |
| 8,518,378 B2 | 8/2013 | Tamarkin et al. | |
| 8,618,081 B2 | 12/2013 | Tamarkin et al. | |
| 2002/0010162 A1 | 1/2002 | Fleischmajer | |
| 2003/0007939 A1 | 1/2003 | Murad | |
| 2003/0077301 A1 | 4/2003 | Maibach et al. | |
| 2004/0076699 A1* | 4/2004 | Chaudhuri ............. | A61K 8/585 424/775 |
| 2006/0084633 A1 | 4/2006 | Iawter et al. | |
| 2006/0275218 A1 | 12/2006 | Tamarkin et al. | |
| 2007/0122463 A1 | 5/2007 | Ko | |
| 2008/0188445 A1 | 8/2008 | Muldoon et al. | |
| 2008/0188446 A1 | 8/2008 | Muldoon et al. | |
| 2008/0312194 A1 | 12/2008 | Ousler et al. | |
| 2009/0214628 A1 | 8/2009 | de Rijk | |
| 2010/0029765 A1 | 2/2010 | Gupta et al. | |
| 2010/0130437 A1 | 5/2010 | Huber et al. | |
| 2011/0020414 A1 | 1/2011 | Kunin | |
| 2011/0121033 A1* | 5/2011 | Horne .................... | A61K 8/368 222/145.1 |
| 2011/0212033 A1 | 9/2011 | Tamarkin et al. | |
| 2012/0070390 A1 | 3/2012 | Phillips et al. | |
| 2012/0082632 A1 | 4/2012 | Phillips et al. | |
| 2012/0087872 A1 | 4/2012 | Tamarkin et al. | |
| 2012/0093876 A1 | 4/2012 | Ousler et al. | |
| 2012/0108527 A1 | 5/2012 | Sawant et al. | |
| 2012/0181201 A1 | 7/2012 | Heggie et al. | |
| 2012/0328549 A1 | 12/2012 | Edelson et al. | |
| 2013/0011342 A1 | 1/2013 | Tamarkin et al. | |
| 2013/0028850 A1 | 1/2013 | Tamarkin et al. | |
| 2013/0045927 A1 | 2/2013 | Dana et al. | |
| 2013/0053353 A1 | 2/2013 | Tamarkin et al. | |
| 2013/0064777 A1 | 3/2013 | Tamarkin et al. | |
| 2013/0189191 A1 | 7/2013 | Tamarkin et al. | |
| 2013/0189368 A1 | 7/2013 | Mosqueira et al. | |
| 2013/0195986 A1 | 8/2013 | Heggie et al. | |

FOREIGN PATENT DOCUMENTS

| | | |
|---|---|---|
| GB | 2474930 A | 5/2011 |
| WO | WO2011138678 A2 | 11/2011 |

OTHER PUBLICATIONS

Instituto Nacional da Propriedade Industrial Search Report for PT 106679 dated Mar. 14, 2014.
Dawn Merton Boothe, Small Animal Clinical Pharmacology Therapeutics, 2nd Edition, Elsevier Saunders:St. Louis, Missouri (2012), p. 251.
International Search Report, PCT/GB2013/052939, International filing date Aug. 11, 2013, Date of mailing of ISR: Jan. 21, 2014.
* cited by examiner

*Primary Examiner* — Nissa Westerberg
(74) *Attorney, Agent, or Firm* — William D. Hare; McNeely Hare & War, LLP

(57) ABSTRACT

The invention relates to a topical suspension formulation that includes a tetracycline, a liquid medium and a polymeric gelling agent. The tetracycline may be in the form of its pharmaceutically acceptable salts, hydrates, or polymorphs and is in a suspended form within the formulation. The liquid medium is selected such that it does not dissolve or substantially minimally dissolves the tetracycline. The gelling agent is a polymeric hydrocarbon gelling agent. Preferably, the tetracycline has a particle size of less than or equal to about 20 microns.

35 Claims, No Drawings

TETRACYCLINE TOPICAL FORMULATIONS, PREPARATION AND USES THEREOF

CROSS-REFERENCE TO RELATED APPLICATIONS

This application claims the benefit of foreign priority under 35 USC 119(a)-(d) of Portuguese Application No. PT106679 filed on Nov. 27, 2012, and such foreign priority application is hereby incorporated by reference.

FIELD OF THE INVENTION

This invention relates generally to a pharmaceutical composition and to a method of preparing it, and to its use in treating various diseases. More particularly, the invention relates to a stable formulation of tetracycline class of compounds, in particular minocycline, and to administering the formulation for topical use in the treatment of infection or inflammation, and for the treatment of dermatological, ophthalmic or neurological diseases.

BACKGROUND OF THE INVENTION

Acne is one of the most common conditions observed in the dermatology clinical practice. It affects nearly all adolescents and young adults to some extent. As suggested by Anthony Mancini, the effects of acne are not limited to skin—acne lesions among adolescents and young adults generally occur at the time of heightened emotional sensitivity and may contribute to significant psychological distress, depression, and even increased risk of suicide (Anthony Mancini; Incidence, prevalence, and pathophysiology of acne; Johns Hopkins Adv Stud Med, volume 8 (4), 100-105 (2008)).

Over the last approximately thirty years, minocycline has been one of the most widely prescribed oral antibiotic treatments for acne. It was first introduced in the US more than thirty years ago and has been available in different dosage forms such as capsules, tablets, lyophilized powder for injection, and suspension (now discontinued). Minocycline has also been formulated as an extended-release powder (PLGA microspheres) for the treatment of periodontal disease. In the UK, minocycline hydrochloride is also available as gel (Dentomycin™ gel) formulation for use in periodontal disease.

Minocycline has a unique biological activity profile: it has both antibacterial and anti-inflammatory properties. It was first launched as a broad spectrum antibiotic for a variety of infectious diseases. Beyond the antibacterial activity, minocycline also has been investigated for new indications, such as its use in neurologic diseases as a potential neuroprotective agent and in ophthalmic diseases. However, minocycline also has been associated with certain adverse effects, especially on prolonged use and at higher doses. Two recent review articles provide a comprehensive summary of minocycline's efficacy and adverse effects in the clinical use.

Leon Kircik (J of Drugs in Dermatology, November 2010) reviewed and compared efficacy and safety of minocycline and doxycycline in moderate-to-severe inflammatory acne patients.

Falk Ochsendorf (Minocycline in Acne Vulgaris—Benefits and Risks, Falk Ochsendorf, American J Clinical Dermatology, 2010) notes that compared with first-generation tetracyclines, minocycline has a better pharmacokinetic profile in man (with practically 100% oral bioavailability), and compared with doxycycline, it is not phototoxic. However, the author suggests that compared with other tetracyclines, minocycline has an increased risk of severe adverse effects: for example, it may induce hypersensitivity reactions affecting the liver, lung, kidneys, or multiple organs (Drug Reaction with Eosinophilia and Systemic Symptoms [DRESS] syndrome) in the first weeks of treatment and, with long-term treatment, may cause autoimmune reactions (systemic lupus erythematosus, autoimmune hepatitis). In addition, CNS symptoms, such as dizziness, are reportedly more frequent with minocycline, as compared with other tetracyclines. Long-term treatment with minocycline may also induce hyper-pigmentation of the skin or other organs. Resistance of *P. acnes* to minocycline also occurs, depending on the prescribing behavior. The author concludes that, considering minocycline's efficacy (through oral administration), its adverse effect profile (from systemic exposure), resistance, price, and alternatives, it is no longer considered the first-line antibacterial in the treatment of acne.

It has been suggested that minocycline, upon repeated oral administration, accumulates in the skin structures and thus imparts its antibacterial and anti-inflammatory activities. Duration of treatment and dose are limited by the potential adverse effects, as described above. These adverse effects are, obviously, directly attributable to its systemic exposure. Systemic exposure is the dose and duration limiting factor in the treatment of acne.

For the treatment of acne, we have appreciated that it would be desirable to have a topical formulation of minocycline for the following reasons: first, it will afford targeted delivery of minocycline at the disease site where it is required and second, and more importantly, a topical administration will significantly reduce (or potentially eliminate) systemic exposure of minocycline. It would be reasonable to expect that lower minocycline systemic exposure would result in minimizing its adverse effects, enable potential for longer-term therapy (longer than 12-weeks that is currently prescribed with oral treatments), and reduce some of the contraindications currently associated with oral formulations.

There have not been any commercially successful topical formulations of minocycline for the treatment of acne reported yet. A major challenge in the development of the topical formulation of minocycline has been its chemical nature: it is unstable in solution form and is also sensitive to moisture, temperature, and light. The most commonly reported impurity is formed through the epimerization of minocycline at C-4 resulting in the formation of the 4-epi-minocycline stereoisomer of minocycline—a minocycline related substance listed in the US and European pharmacopeias with defined limits. The structures of 4-epiminocycline and minocycline are provided below:

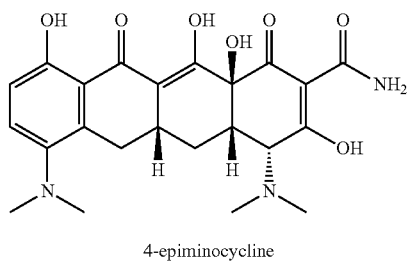

4-epiminocycline

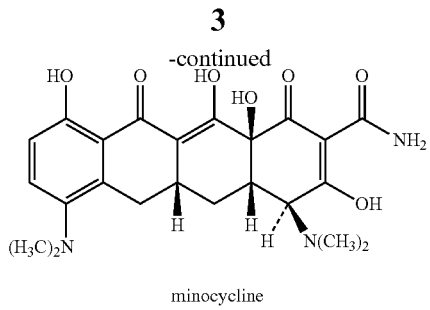

minocycline

Consequently, it has not been possible to formulate a topical formulation that contains minocycline in a stable solubilized form. Periodontal topical minocycline gel (Dentomycin gel; 1% minocycline gel, in clinical use in the UK) must be stored at refrigerated temperatures, presumably due to stability issues. Following is a brief description of related art in the field.

US patent application US 2008/0188446A1 (and references therein) succinctly describes prior art in the field and concludes that none of the past attempts have adequately addressed the stability of tetracycline and provided a stable topical formulation for this class of compounds. US2008/0188446A1 describes a formulation for minocycline and doxycycline incorporating cyclomethicone, ST-Elastomer 10 and isopropyl myristate. While this formulation might provide some stability to the API, it contains isopropyl myristate, a known comedogenic substance thus limiting its usefulness in the treatment of acne.

WO 2011/039637A2 and US patent application 2010/0310476A1 describe an elaborate method and complex constituents for foam formulation of tetracyclines. A foam formulation, as claimed in the above applications, whilst having some stability might not deliver a consistent amount of the active substance to the site of application over the duration of treatment. It also requires an extra layer of complexity for the delivery of drug formulation using a foam pump. Similarly, US 2011/0281827 A1 and US 2012/0087872 A1 require use of a pump to deliver a foam formulation.

US patent application 2012/0093876A1 describes suspension formulations of minocycline hydrochloride in oil and in petrolatum for ophthalmic use. It concludes that minocycline hydrochloride in an oil suspension is unstable after two months with change in color. However, a petrolatum based ointment suspension was considered stable enough for further investigation by these investigators. We have discovered that, surprisingly, minocycline can in fact be stabilized in an oil containing suspension, for example a suspension oil gel formulation (details of which are described more fully below) is quite stable at ambient temperatures for one year the stability testing was conducted.

We have appreciated there remains a medical need for a stable, practical, commercially feasible and easy to manufacture and easy to use topical formulation of tetracycline class of compounds, especially but not exclusively comprising minocycline and doxycycline, and particularly comprising minocycline, which formulation can be administered to a patient in need for the treatment of infections or inflammation and for the treatment of dermatologic, ophthalmic or neurological disease.

SUMMARY OF THE INVENTION

In one general aspect, the invention relates to a topical suspension formulation comprising a tetracycline, a liquid medium and a polymeric gelling agent. The tetracycline may be in the form of a pharmaceutically acceptable salt, hydrate, or polymorph thereof and is in a suspended form within the formulation. The liquid medium is selected such that it does not dissolve or substantially minimally dissolves the tetracycline. The gelling agent is preferably a polymeric hydrocarbon gelling agent. The tetracycline preferably has a particle size (D90) of less than or equal to about 20 microns.

A liquid medium which does not dissolve or substantially minimally dissolves the tetracycline is suitably one which results in less than 5% of the tetracycline active ingredient being dissolved in the medium at room temperature after 2 hours, as measured by HPLC.

According to one aspect, the present invention provides a topical suspension formulation comprising:

a tetracycline, or a pharmaceutically acceptable salt, hydrate, or polymorph thereof in a suspended form within the formulation;

a liquid medium that does not dissolve or substantially minimally dissolves the tetracycline; and a polymeric hydrocarbon gelling agent.

Preferably, the particle size of the tetracycline is less than or equal to 20 microns.

In another aspect, the invention provides a topical minocycline suspension formulation for treating an individual afflicted with acne vulgaris, the composition consisting essentially of a pharmaceutically effective amount of minocycline, a hydrophobic liquid medium that does not dissolve or minimally dissolves tetracycline, and a polymeric hydrocarbon gelling agent to thicken the composition, wherein:

the hydrophobic liquid medium is characterized as (a) resulting in less than 5% of the tetracycline active ingredient being dissolved in the medium at room temperature after 2 hours as determined by HPLC, and/or (b) results in less than 4% of 4-epi-minocycline (when minocycline is used as the active ingredient) when stored for 1 month at room temperature, as determined by HPLC.

In a further aspect, the invention provides a topical suspension formulation comprising:

a tetracycline, or its pharmaceutically acceptable salts, hydrates, or morphs in a suspended form within the formulation;

anon-comedogenic, hydrophobic liquid medium that does not dissolve or substantially minimally dissolves the tetracycline; and a polymeric hydrocarbon gelling agent to thicken the suspension.

In another aspect, the invention provides a method of treating an infection or inflammation of the skin, the method comprising topically administering to a subject in need of such treatment a suspension formulation according to the invention.

The invention also provides a method of treating an infection or inflammation of the skin wherein the disease is characterized as acne, particularly acne vulgaris, or rosacea.

The invention also provides a method of treating an ophthalmic disease or condition, the method comprising topically administering to a surface of the eye of a subject in need of such treatment a suspension formulation according to the invention.

In the topical suspension formulation of the invention, the tetracycline is preferably minocycline, especially crystalline minocycline free base.

The invention also provides a formulation according to the invention as defined herein for use as a medicament, especially for use in treating infection or inflammation of the skin, such as acne, particularly acne vulgaris, or rosacea. The formulation of the invention as defined herein may also be used in treating an ophthalmic disease or condition.

In a preferred aspect, the formulation of the invention does not comprise petrolatum or petroleum jelly. The formulation of the invention is preferably in the form of a gel. Preferred formulations can be described as suspension oil gel formulations. Preferred formulations are easily spreadable when applied to the skin with a finger-tip, and can also be easily dispensed from a squeezable tube.

Preferably, the topical suspension formulation may include one or more of the following features. For example, the tetracycline may have a D90 particle size that has a value that is from about 4 microns to about 10 microns. The tetracycline may have a D90 particles size that has a value that is from about 4 microns to about 10 microns and a D50 particle size that has a value that is from about 1 micron and about 5 microns. The tetracycline may have a D90 particle size that has a value that is from about 4 microns to about 10 microns, a D50 particle size that has a value that is from about 1 micron to about 5 microns, and a D10 particle size that has a value that is from about 0.5 microns to about 1.5 microns.

D10, D50, and D90 represent the particle size distribution and refer to under 10%, under 50%, and under 90% particle volume distribution, respectively, of the total particles in a sample. As will be understood by those in the art, the particle size distribution is generally measured using laser diffraction. In the present application, the particle size distribution was determined using a Malvern® MasterSizer 2000 LASER diffractor.

The tetracycline may be minocycline or doxycycline, or a pharmaceutically acceptable salt or hydrate or polymorph thereof. The concentration of the minocycline in the composition may be from about 0.05% to about 10% (by weight) of the total composition. The minocycline may be in any suitable form, with one preferred form being crystalline minocycline free base.

An advantage of the present formulation is its stability compared to prior art formulations, particularly with respect to discoloration over time and the amount of impurities, including breakdown products of the active material, such as 4-epi-minocycline. The formulations of the invention are stable over at least 1 year (with respect to the above features) at ambient temperature (25° C.).

The topical suspension formulation that includes minocycline preferably has a concentration of 4-epi minocycline that is not more than 4% after storage for 6 months at real-time (25° C./60% relative humidity (RH)) and at accelerated (40° C./75% RH) stability conditions, as determined by HPLC analysis. Or the topical suspension formulation that includes minocycline has a concentration of 4-epi minocycline in the minocycline suspension formulation when stored at 40° C./75% RH for one month that results in less than 3% of 4-epi-minocycline, as determined by HPLC analysis. Preferably, the topical suspension formulation that includes minocycline has a concentration of 4-epi minocycline in the minocycline suspension formulation when stored at 40° C./75% RH for three months results in less than 4% of 4-epi-minocycline, as determined by HPLC analysis. Further, the suspension formulation that includes minocycline may have a concentration of no more than 4% 4-epi minocycline after storage for 12 months at real-time (25° C./60% RH) stability conditions, as determined by HPLC analysis. The percentages expressed above are by weight of the minocycline.

In the topical suspension formulation, the liquid medium may be a non-comedogenic liquid medium. The non-comedogenic liquid medium may be one or more of a mineral oil, a light mineral oil, a minimally comedogenic oil and an additional non-comedogenic oil. The non-comedogenic liquid medium may, for example, be mineral oil.

The non-comedogenic liquid medium may be characterized as (a) resulting in less than 5% of the tetracycline active ingredient being dissolved in the medium at room temperature after 2 hours, as measured by HPLC, and/or (b) resulting in less than 4% of 4-epi-minocycline, if minocycline is used as the active ingredient, when stored for 1 month at room temperature, as measured by HPLC. Preferably, the mineral oil may constitute about 70% to about 90% of the suspension formulation. Or the mineral oil may constitute at least 90% of the suspension formulation. Or the mineral oil may constitute at least 70% of the suspension formulation.

The polymeric hydrocarbon gelling agent can be any suitable gelling agent, and is preferably Versagel®M (200, 500, 750 or 1600) or a gel comprising an oil and one or more gelling polymers.

The topical suspension formulation may be free of a skin penetration enhancing agent or an excipient that functions primarily or solely as a skin penetration enhancer. In a preferred aspect, the formulation of the invention is free of isopropyl myristate.

The formulation is preferably also free of a compound that results in dissolution of the tetracycline active ingredient. The compound that results in dissolution of the tetracycline active ingredient may include one or more of water, hydrophilic solvents and emollient esters.

The liquid medium or carrier may be a combination of a non-comedogenic medium or carrier and a comedogenic medium or carrier with the non-comedogenic medium or carrier being present in a greater amount than the comedogenic medium or carrier.

The topical suspension formulation is preferably not a foam, and is also preferably nonfoamable. It is preferably free of a foaming adjuvant. The formulation of the invention is preferably free of propellant.

The topical suspension composition may further include one or more of a sunscreen agent, a fragrance and a colorant or dye.

The topical suspension formulation may further include a pharmaceutically effective amount of a retinoid selected from tretinoin, adapalene and tazarotene.

In a preferred aspect of the invention, the formulation is free of silicone thickening agents, in particular free of hydrophobic, non-hygroscopic silicone thickening agents.

The topical suspension formulation may be used in a method of treating an infection or inflammation of the skin, the method may include topically administering to a subject in need of such treatment one of the suspension formulations disclosed herein. The disease may be characterized as being acne or rosacea.

The topical suspension formulation may be used in a method of treating an ophthalmic disease or condition, the method comprising topically administering to a surface of the eye of a subject in need of such treatment one of the suspension formulations disclosed herein.

In another embodiment, the topical suspension formulation may consist essentially of a pharmaceutically effective amount of minocycline or a pharmaceutically acceptable salt, hydrate, or polymorph thereof, a non-comedogenic liquid medium that does not dissolve or minimally dissolves tetracycline, and a gelling agent to thicken the composition and optionally one or more of 4-epi minocycline, colorants, dyes, fragrances and a sunscreen material. The formulation may include one or more of the features described above or herein.

The topical suspension formulation may consist of a pharmaceutically effective amount of minocycline or a pharmaceutically acceptable salt, hydrate, or polymorph thereof, a non-comedogenic liquid medium that does not dissolve or minimally dissolves minocycline, and a gelling agent to thicken the composition. The formulation may include one or more of the features described above or herein.

The topical suspension formulation may consist of a pharmaceutically effective amount of minocycline or a pharmaceutically acceptable salt, hydrate, or polymorph thereof, a non-comedogenic liquid medium that does not dissolve or minimally dissolves minocycline, and a gelling agent to thicken the composition and 4-epi minocycline, and optionally one or more of a comedogenic liquid medium present at an amount less than the non-comedogenic liquid medium, colorants, dyes, fragrances and sunscreen materials. The formulation may include one or more of the features described above or herein.

In another general aspect, there is provided a topical minocycline suspension composition for treating an individual afflicted with acne vulgaris. The composition consists essentially of a pharmaceutically effective amount of minocycline or a pharmaceutically acceptable salt, hydrate, or polymorph thereof, a liquid medium that does not dissolve or minimally dissolves tetracycline, and a gelling agent to thicken the composition. The liquid medium is characterized as (a) resulting in less than 5% of the tetracycline active ingredient being dissolved in the medium at room temperature after 2 hours, and/or (b) results in less than 4% of 4-epi-minocycline (when minocycline is used as the active ingredient) when stored for 1 month at room temperature. The formulation may include one or more of the features described above or herein.

In another general aspect there is provided a topical minocycline composition for treating acne vulgaris. The composition consists essentially of a pharmaceutically effective amount of minocycline or a pharmaceutically acceptable salt, hydrate, or polymorph thereof, a hydrophobic liquid medium that does not dissolve or minimally dissolves minocycline, and a polymeric hydrocarbon gelling agent to thicken the composition. Preferably, the composition contains less than 4% of 4-epi minocycline after storage for 6 months at real-time (25° C./60% RH) and at accelerated (40° C./75% RH) stability conditions, as determined by HPLC analysis. The carrier agent may include a hydrophobic solvent which can keep minocycline in suspended form such that the solubility of minocycline in suspended form is no more than 5%. Thehydrophobic liquid medium may be characterized as (a) resulting in less than 5% of the tetracycline active ingredient being dissolved in the medium at room temperature after 2 hours as determined by HPLC, and/or (b) results in less than 4% of 4-epi-minocycline (when minocycline is used as the active ingredient) when stored for 1 month at room temperature as determined by HPLC.

In another general aspect, the invention relates to a topical suspension formulation that includes a tetracycline or a pharmaceutically acceptable salt, hydrate, or polymorph thereof, a non-comedogenic, hydrophobic liquid medium and a polymer hydrocarbon gelling agent. The tetracycline, or its pharmaceutically acceptable salts, hydrates, or morphs is in a suspended form within the formulation. The non-comedogenic, hydrophobic liquid medium does not dissolve or substantially minimally dissolves the tetracycline. The polymeric hydrocarbon gelling agent thickens the suspension.

The topical suspension formulation may include one or more of the features described herein.

Preferred aspects of the invention are set forth in the description below, it being understood these are given to illustrate the invention and are not limiting thereon. Other features and advantages of the invention will be apparent from the description and claims.

DETAILED DESCRIPTION OF THE INVENTION

The present invention is related to a tetracycline suspension formulation for topical administration comprising an active compound belonging to tetracycline class of compounds, or a pharmaceutically acceptable salt or hydrate or polymorph thereof, substantially stabilized as a suspension in an appropriate liquid medium that the tetracycline has no or substantially minimal solubility in, and that is suitable for topical application to humans in need of a treatment for infection or inflammation or dermatologic or ophthalmic disease. The suspension medium is preferably comprised of a non-comedogenic liquid, suitable for topical application and, for example, selected from the US FDA's list of Inactive Ingredients Guide. In a particularly preferred embodiment, the suspension medium is selected from mineral oils or similar oils. In a more preferred embodiment, the suspension medium is mixed with a gelling agent comprising a gelled mineral oil, such as commercially available Versagel®M (Versagel®M contains a mixture of white mineral oil (90-100%)+Ethylene/Propylene/Styrene copolymer (2.5-10%)+Butylene/Ethylene/Styrene copolymer (1-2.5%), and butylated hydroxyl toluene (<0.1%).

A comedogenic ingredient is variously defined as an ingredient that (a) tends to clog pores, especially by the formation of blackheads, and (b) tends to produce or aggravate acne. It is reported in the literature that comedogenic excipients may vary in their comedogenicity with some excipients being highly comedogenic, some being moderately comedogenic and others being mildly comedogenic. As used herein a non-comedogenic ingredient is one that does not tend to clog pores and/or produce or aggravate acne.

In one aspect, the present invention is related to a topical formulation of a tetracycline class of compounds comprising at least one tetracycline or a pharmaceutically acceptable salt or hydrate or polymorph thereof stabilized as a suspension in an appropriate medium in which the tetracycline has no or substantially minimal solubility, and that is suitable for topical application to humans in need of a treatment for infection or inflammation or ophthalmic disease. Preferably, the tetracycline class of compounds includes minocycline and doxycycline. More preferably, the tetracycline is specifically minocycline or a pharmaceutically acceptable salt, hydrate, or polymorph thereof. In a preferred aspect, the suspension medium is comprised of a non-comedogenic liquid medium, suitable for topical application and preferably selected from the US FDA's list of Inactive Ingredients Guide. Particularly preferably, the suspension medium is selected from mineral oils or similar oils. The suspension medium may be mixed with a gelling agent comprising of gelled mineral oil, such as commercially available Versagel®M (a mixture of white mineral oil+ethylene/propylene/styrene copolymer+butylene/ethylene/styrene copolymer+butylated hydroxytoluene as an optional anti-oxidant).

The present invention is also related to a method of treating dermatological or ophthalmic diseases by administering the tetracycline suspension formulation to humans or animals in need of such treatment. In one aspect, the tetracycline suspension formulation is administered twice-daily to subjects in need of such treatment. In another aspect, the suspension formulation is administered once-daily at night before bedtime to the patients in need of such treatment. Alternatively, the suspension formulation is administered at night before bedtime followed by topical administration of benzoyl peroxide in the morning to a patient in need of such treatment.

The tetracycline class of compounds may be combined with additional anti-acne active agents such as the retinoid class of compounds, in a suspension formulation. Examples of the retinoid ant-acne ingredient include adapalene, tretinoin, and tazarotene. Adapalene is marketed in topical gels and lotions at strengths ranging from 0.1% to 0.3%. One example of a topical adapalene product is Differin™ by Galderma. Tretinoin is marketed in topical creams and gels at strengths of 0.02%, 0.04% and 0.1%. One example of a topical tretinoin is Retin-A™. Tazarotene is marketed in topical gels and creams at strengths of 0.05% and 0.1%. Examples of topical tazarotene products are Avage™ and Tazorac™ by Allergan. The above strengths of these anti-acne compounds are pharmaceutically effective for treating acne, although strengths other than these may be pharmaceutically effective as well.

In yet another aspect the tetracycline class of compounds is combined with a sunscreen in a suspension formulation.

The tetracycline suspension formulation may consist of the tetracycline active ingredient, the non-comedogenic liquid medium and the gelling agent. The tetracycline active ingredient may be, for example, minocycline or doxycycline or a pharmaceutically acceptable salt, hydrate, or polymorph thereof. The non-comedogenic liquid medium may be a mineral oil. The gelling agent may be a gelled mineral oil or one or more gelling polymers. It is understood that a composition that consists of the tetracycline active ingredient, the non-comedogenic liquid medium and the gelling agent may over time include some degradation product of the tetracycline active ingredient. Thus, in another aspect, the composition may consist of the tetracycline active ingredient, the non-comedogenic liquid medium, the gelling agent and some degradation product of the tetracycline active ingredient. It also is understood that a composition that consists of the tetracycline active ingredient, the non-comedogenic liquid medium and the gelling agent may also include a comedogenic liquid medium present in an amount that does not result in measurable or noticeable comedogenic effects to individuals using the formulation with the comedogenic agent present. As explained above, over time the formulation may include some degradation product of the tetracycline active ingredient. Thus, the composition may consist of the tetracycline active ingredient, the non-comedogenic liquid medium, the gelling agent, an amount of a comedogenic liquid medium and some degradation product of the tetracycline active ingredient.

The tetracycline suspension formulation may consist essentially of the tetracycline active ingredient, the non-comedogenic liquid medium to act as a carrier of the tetracycline active ingredient in the form of a suspension, and the gelling agent to thicken the composition. The tetracycline active ingredient may be, for example, minocycline or doxycycline or a pharmaceutically acceptable salt, hydrate, or polymorph thereof. The non-comedogenic liquid medium may be a mineral oil. The gelling agent may be a gelled mineral oil or one or more gelling polymers. It is understood that the tetracycline suspension formulation that consists essentially of the tetracycline active ingredient, the non-comedogenic liquid medium to act as a carrier of the tetracycline active ingredient in the form of a suspension, and the gelling agent to thicken the composition, may still further include additional ingredients that are not intended to function as a carrier or thickening agent. For example, the composition may further include colorants, dyes, fragrances and sunscreen materials. Examples of sunscreen agents that may be used include zinc oxide; titanium dioxide benzophenones such as avobenzone, oxybenzone and dioxybenzone; octyl salicylate octocrylene; and aminobenzoic acid.

The tetracycline suspension formulation may consist essentially of the tetracycline active ingredient, the non-comedogenic liquid medium to act as a carrier of the tetracycline active ingredient in the form of a suspension, a small amount of a comedogenic liquid medium to act as a carrier of the tetracycline active ingredient, and the gelling agent to thicken the composition. The tetracycline active ingredient may be, for example, minocycline or doxycycline or a pharmaceutically acceptable salt, hydrate, or polymorph thereof. The non-comedogenic liquid medium may be a mineral oil. The gelling agent may be a gelled mineral oil or one or more gelling polymers. It is understood that the tetracycline suspension formulation that consists essentially of the tetracycline active ingredient, the non-comedogenic liquid medium to act as a carrier of the tetracycline active ingredient in the form of a suspension, the comedogenic liquid medium to act as a carrier of the tetracycline active ingredient in the form of a suspension, and the gelling agent to thicken the composition, may still further include additional ingredients that are not intended to function as a carrier or thickening agent. For example, the composition may further include colorants, dyes, fragrances and sunscreen materials. Examples of sunscreen agents that may be used include zinc oxide; titanium dioxide benzophenones such as avobenzone, oxybenzone and dioxybenzone; octyl salicylate octocrylene; and aminobenzoic acid. The composition that consists essentially of the tetracycline active ingredient, the non-comedogenic liquid medium to act as a carrier of the tetracycline active ingredient in the form of a suspension, the comedogenic liquid medium to act as a carrier of the tetracycline active ingredient in the form of a suspension, and the gelling agent to thicken the composition, may still further include the degradation product 4-epi-minocycline.

The tetracycline suspension formulation of the invention contains at least one tetracycline or a pharmaceutically acceptable salt or hydrate or polymorph thereof, substantially stabilized as a suspension, as determined by HPLC analyses of the samples stored at real-time (25° C./60% RH) and at accelerated (40° C./75% RH) stability conditions. Preferably, at least 90% of the active tetracycline compound is retained after 6 months of storage at the real-time and accelerated stability conditions, as described above. More preferably, at least 90% of the active tetracycline compound is retained after 12 months of storage at the real-time stability conditions, as described above. Preferably, when the tetracycline suspension contains minocycline as an active tetracycline, stabilization is also determined by the levels of 4-epi-minoccyline, as determined by HPLC analysis. Preferably, the minocycline suspension formulation contains no more than 6% of 4-epi minocycline after storage for 6 months at real-time and accelerated stability conditions, as described above. Preferably, the minocycline suspension formulation contains no more than 5% of 4-epi minocycline after storage for 6 months at real-time and accelerated stability conditions, as described above. Preferably, the minocycline suspension formulation contains no more than 4% of 4-epi minocycline after storage for 6 months at real-time and accelerated stability conditions, as described above. More preferably, the minocycline suspension formulation contains no more than 3% of 4-epi minocycline after storage for 6 months at real-time and accelerated stability conditions, as described above. Yet more preferably, the minocycline suspension formulation contains no more than 4% of 4-epi minocycline after storage for 12 months at real-time stability conditions, as described above.

The suspension formulation of the invention may contain 0.01% to 20% (weight by weight) of the active tetracycline compound. Preferably, the suspension formulation contains 0.05% to 10% (weight by weight) of the active tetracycline compound.

The tetracycline suspension formulation refers to a formulation that suitably contains less than 5% (weight by weight) of the dissolved active tetracycline. Preferably, the tetracycline suspension formulation contains less than 1% (weight by weight) of the dissolved active tetracycline. More preferably, the tetracycline suspension formulation contains less than 0.5% (weight by weight) of the dissolved active tetracycline. The amount of dissolved active ingredient is determined by HPLC analysis.

The suspension formulation of the invention preferably comprises specific particle size of the active tetracycline. Preferably, the particle size of suspended active tetracycline is less than or equal to 20 microns. In a preferred aspect, 90% of the suspended tetracycline particles are less than 10 microns in size. Preferably, the particle size ranges from about 2 microns to about 10 microns, more preferably from about 3 microns to about 8 microns, as a range for optimal penetration of the tetracycline active ingredient into the skin. For a particle size above about 8 to 10 microns there is believed to be very little if any penetration into the skin and for a particle size below about 2 to 3 microns there may be too much penetration into the skin such that the blood levels of minocycline are higher than desired. Further, if the particle size is too small, there is increased likelihood that some of the tetracycline active ingredient may dissolve and be subject to degradation. Thus, preferably, the D90 value may be a value that is from about 2 microns to about 10 microns. Therefore the D90 may be 2 microns, 3 microns, 4 microns, 5 microns, 6 microns, 7 microns, 8 microns, 9 microns or 10 microns. An important factor in the particle size selection is that a sufficient amount of the particles is from about 2 to about 8 microns to sufficiently penetrate into the skin.

Formulations were prepared using two lots of minocycline active ingredient of different particle size distributions. Both lots are believed to be suitable for use as the minocycline active ingredient in a topical suspension formulation according to the invention. The particle size distributions were as follows:

| Particle size Parameter | Lot 1 (Batch-00079) (microns) | Lot 2 (Batch-00002) (microns) |
|---|---|---|
| D90 | 8.94 | 4.51 |
| D50 | 4.15 | 2.00 |
| D10 | 1.00 | 0.69 |

The inventors have made formulations according to Example 1 using the two lots of minocycline ingredient described above. The particle size parameters measured using a Malvern Mastersizer 2000 after storage for the indicated times are provided below.

| Particle size Parameter | Suspension formulation with Lot 1 minocycline (Batch 3663-46) after approximately one year storage at 25° C./60% RH (microns) | Suspension formulation with Lot 2 minocycline (Batch 3663-65) After approximately 3 month storage at room temp (microns) |
|---|---|---|
| D90 | 9.72 | 3.68 |
| D50 | 4.57 | 2.01 |
| D10 | 1.35 | 0.95 |

The data above indicates that the particle size of the minocycline stays substantially the same during formulation and after storage.

Therefore, in one aspect of the invention, the tetracycline active ingredient has a D90 value that is a single value of from about 4 to about 10 microns. For example, the D90 may be 4 microns, 5 microns, 6 microns, 7 microns, 8 microns, 9 microns, or 10 microns, or fractional values in between as will be understood by the skilled person. In another aspect of the invention, the tetracycline active ingredient has a D90 value that is a single value of from about 4 to about 10 microns and a D50 value that is a single value of from about 1 to about 5. In another aspect of the invention, the tetracycline active ingredient has a D90 value that is a single value of from about 4 to about 10, a D50 value that is a single value of from about 1 to about 5, and a D10 value that is a single value of from about 0.5 to about 1.5.

The particle size distribution described above should be understood to refer to both the particle size of the active ingredient used in the formulation as well as the particle size of the active ingredient present in the suspension formulation. Therefore, a loose agglomeration of particles with a D90, D50, D10 or general particles size that breaks into the particles when shaken or formulated is intended to be included in the invention because the particles in the suspension are within the particle size described herein and are expected to provide the desired therapeutic effect. The particles to be used in the formulation can be gently shaken to reduce any intentionally or unintentionally formed agglomerations. The particle size and particle size distribution of the tetracycline particles may be measured using a Malvern Mastersizer. This measurement may be made of the active ingredient prior to formulation and of the suspension formulation itself.

The tetracyclines include all related compounds from this generic class of compounds, as would be known to a person skilled in the art. Preferably, the tetracycline are is doxycycline or minocycline, or their pharmaceutically acceptable salts, hydrates, or polymorphs. More preferably, the active tetracycline refers to minocycline or its pharmaceutically acceptable salts, hydrates, or polymorphs. The suspension formulation preferably contains 0.01% to 20% (weight by weight) of the active tetracycline compound. More preferably, the suspension formulation contains 0.05% to 10% (weight by weight) of the active tetracycline compound. Yet more preferably, the suspension formulation contains 0.1% to 10% (weight by weight) of minocycline or its pharmaceutically acceptable salts, hydrates, or polymorphs.

Minocycline is sparingly soluble in water, slightly soluble in alcohol, practically insoluble in chloroform and in ether, and soluble in solutions of alkali hydroxides and carbonates. Minocycline is highly sensitive and should be stored in airtight containers and protected from light to prevent degradation. The instability of minocycline was described is US 20130064777 to which reference can be made for further details, and the contents of which are incorporated herein in their entirety for the selection of excipients for use with tetracyclines, where a compatibility study is reported that demonstrated that different hydrophilic solvents were incompatible with minocycline whereas hydrophobic emollients and waxes were compatible with minocycline, except for pomegranate seed oil. US 20130064777 also reports that all fatty alcohols, as well some fatty acids (such as stearic acid, oleic acid, palmitic acid) surfactants (sucrose fatty esters however not all of them dissolved in oil) and some additives (aerosil and menthol) were compatible with minocycline. Isostearic acid, Ethocel™ and titanium dioxide polysorbates, sorbitan esters (Span®), polyoxyethylene alkyl ethers (Brij™), PEG stearates (Myrj™) were reported to not be compatible with minocycline. The publication also reports that addition of water caused rapid degradation of minocycline with addition of antioxidants (alpha-tocopherol, BHA/BHT and propyl gallate) not preventing such degradation. The publication concludes that compatible excipients became incompatible in the presence of water and addition of antioxidants did not remedy this result.

This invention also relates to the use of a non-comedogenic liquid medium that does not solubilize the tetracycline class of compounds, for the preparation of a suspension formulation. Preferably, the non-comedogenic liquid medium for suspension formulation refers to mineral, light mineral, other non-comedogenic oils and minimally comedogenic oils. In a preferred aspect, the non-comedogenic liquid medium for suspension formulation refers to mineral oil. In a preferred aspect, the tetracycline suspension formulation contains 70% to 90% mineral oil. In a more preferred aspect, the tetracycline suspension formulation contains approximately 90% mineral oil. The mineral oil may be made up of a combination of mineral oil itself and mineral oil that is a component of a second component, such as a gelling agent in the form of the polymeric hydrocarbon gel.

Preferably, the polymeric hydrocarbon gelling agent is a mixture of a mineral oil and one or more copolymers based on one or more monomers selected from alkene monomers, particularly $C_1$-$C_{10}$, or $C_1$ to $C_6$, or $C_2$ to $C_4$ alkene monomers, and phenylalkene monomers, particularly $C_1$-$C_{10}$, or $C_1$ to $C_6$, or $C_2$ to $C_4$ phenylalkene monomers, or is a gel comprising an oil and one or more gelling polymers.

The one or more copolymers may comprise an ethylene/propylene/styrene copolymer, and/or the one or more copolymers may comprise a butylene/ethylene/styrene copolymer.

The suspension formulation may further comprise an anti-oxidant, particularly butylated hydroxytoluene.

In a preferred aspect, the polymeric gelling agent comprises ethylene/propylene/styrene copolymer and butylene/ethylene/styrene copolymer and butylated hydroxytoluene as an optional anti-oxidant.

Preferably, the gelling agent comprises a polymeric hydrocarbon gel such as commercially available Versagel®M (Versagel contains a mixture of white mineral oil (90-100%)+Ethylene/Propylene/Styrene Copolymer (2.5-10%)+Butylene/Ethylene/Styrene Copolymer (1-2.5%)) or such similar gelling agents. Surprisingly no aggregates of the active tetracycline compound were observed over a period of approximately one year with the use of specific particle size of the active tetracycline, as described above.

Other non-comedogenic liquid media may be chosen instead of or in addition to mineral oil. The non-comedogenic liquid media is selected based on its ability to keep the tetracycline in suspension, i.e., the non-comedogenic liquid minimally solubilizes or does not solubilize the tetracycline compound. By selecting a liquid medium that minimally solubilizes or does not solubilize the tetracycline compound, the stability of the tetracycline compound is improved. The procedure for determining whether or not a particular liquid medium minimally solubilizes or does not solubilize the tetracycline compound is well-known. Specifically, a suitable liquid media is selected by (1) testing the solubility of the tetracycline active agent in various liquid media solvents, (2) identifying those that do not solubilize or minimally solubilize the tetracycline active agent followed by (3) inclusion in the composition of such liquid media solvents that do not solubilize or minimally solubilize the active agent. Preferably, the tetracycline compound is completely insoluble or minimally soluble in the composition that includes the liquid media. Examples of suitable liquid medium include mineral oil, paraffin oil, fatty acids such as castor oil/peanut oil, sunflower oil, light mineral oil, squalene, squalane, triglycerides, monoesters and di-esters, fractionated coconut oil and silicone oil. It should be understood that the above testing protocol for the non-comedogenic liquid media can be applied to determine whether a minimally comedogenic liquid media will be suitable with respect to extent of solubility of the tetracycline ingredient in the medium.

In particular, the non-comedogenic liquid medium may include any liquid medium that (a) results in less than 5% of the tetracycline active ingredient being dissolved in the medium at room temperature after 2 hours, and/or (b) results in less than 4% of 4-epi-minocycline (when minocycline is used as the active ingredient) when stored for 1 month at room temperature. It should be understood that the above testing specification for the non-comedogenic liquid medium can be applied to determine whether a minimally comedogenic liquid media will be suitable with respect to extent of solubility of the tetracycline ingredient in the medium and formation of the 4-epi-minocycline.

In addition to including non-comedogenic liquid medium excipients, it should be understood that the formulation can also include comedogenic liquid medium excipients. For example, it is reported that mildly comedogenic excipients may be included in a formulation and not create a problem when used at dilute concentrations. Such mildly comedogenic excipients include avocado oil, corn oil, D&C Red number 4, 6, 7 or 8, glyceryl stearate, lanolin, lanolin alcohol, lauryl alcohol, and safflower oil. Other comedogenic liquid medium that have a high or medium comedogenic ranking may, of course, be used in the formulation in amounts small enough to not cause acne.

One objective of the invention is to prevent significant degradation of the tetracycline active ingredient that occurs when the compound is in solution. To avoid this category of degradation, the formulations typically do not include water, hydrophilic solvents or emollient esters. The formulations therefore may be characterized as being free of water, and/or free of a hydrophilic solvent and/or free of an emollient ester in an amount sufficient to cause solubilization of the tetracycline or degradation of the tetracycline.

The formulations may also be characterized as being free of a skin penetration enhancer or an excipient that functions primarily or solely as a skin penetration enhancer. In particular, the formulation is free of a penetration enhancer in an amount that causes the tetracycline to enter the blood stream at an undesirable level. In other words, the formulation may include an excipient that minimally functions as a penetration enhancer but is present primarily for another purpose, e.g., to thicken the formulation, or as a carrier, but the penetration enhancer may not cause the tetracycline to be present in the blood stream at an undesirable level.

The following examples are intended to illustrate the invention, without limiting it in any way.

EXAMPLE 1

A tetracycline suspension formulation for topical administration was prepared using the ingredients as listed in Table 1 below.

TABLE 1

| Ingredient | % (weight/weight) |
|---|---|
| Minocycline free base (crystalline) | 1 |
| Mineral oil | 30 |
| Versagel ® M-750 | 69 |

Minocycline free base crystalline (having desired particles size distribution) was added to mineral oil and the mixture stirred for about 30 minutes. Versagel® M-750 was then added slowly and the suspension stirred for another 30 minutes.

Suspension formulation as described above was prepared at different scales (1 kg and 5 kg) and with different strengths of minocycline. Suspension homogeneity was confirmed by HPLC analyses of multiple samples from different locations of the mixing vessel. To determine packaging compatibility, suspension formulation from Example 1 was packed in glass jars and aluminum and laminate tubes appropriate for packaging topical formulations. Samples of the suspension formulation were stored for real time and accelerated stability studies according to ICH stability storage guidelines. USP HPLC method was used to determine minocycline and related substances. Particle size analyses of the suspension formulation after approximately one year at 25° C./40% RH showed no agglomeration or changes, as compared with the particle size distribution of the starting minocycline drug substance.

EXAMPLE 2

A tetracycline suspension formulation for topical administration was prepared using the ingredients as listed in Table 2 below.

TABLE 2

| Ingredient | % (weight/weight) |
|---|---|
| Minocycline free base (crystalline) | 1 |
| Capric/Caprylic triglycerides | 15 |
| Versagel ® M-750 | 84 |

Minocycline free base crystalline (having desired particles size distribution) was added to Capric triglycerides and the mixture stirred for about 30 minutes. Versagel® M-750 was then added slowly and the suspension stirred for another 30 minutes. Samples of the suspension formulation were tested for stability at 25 and 40 degrees Celsius over a period of three months. USP HPLC method was used to determine minocycline and related substances. Suspension formulation samples were first dissolved in THF before dilutions for HPLC analyses.

Specific embodiments of the invention are described below as examples. These examples are intended for the purpose of illustration only and should not be taken in any way to limit the scope of the present invention.

Stability Studies

Minocycline suspension formulations prepared in Examples 1 and 2 were tested for stability by determining minocycline and 4-epi-minocycline. Samples from Example 1 showed that minocycline remained stable over a period of six months at 40° C. while samples from Example 2 showed a change in color, indicating formation of degradation products. Moreover, samples from Example 2 showed settling after 3 months at 40° C. Extent of epimerization at C-4 of minocycline is one of the key stability indicating impurities; samples from Example 1 showed less than 1% 4-epi minocycline over a period of six months at 40° C.

Minocycline suspension formulation from Example 1 was packed in aluminum and laminate tubes for stability and packaging compatibility studies according to the ICH stability protocols (Table 3). The suspension formulation showed excellent stability over a period of six months at accelerated (40° C./75% RH) and over one year at real-time conditions (25° C./60% RH). These stability and packaging compatibility studies are ongoing; based on existing stability data, a shelf life of at least eighteen months is projected for the minocycline suspension described in Example 1.

TABLE 3

Batch 3663-46 (1% minocycline gel) - ICH stability and compatibility studies

| Condition | Time (Months) | Minocycline % Label Claim | 4-Epi-minocycline Area % | Total Impurities (including 4-epi) |
|---|---|---|---|---|
| 25° C./ 60% RH | 0 | 98.48 | 0.14 | 0.30 |
| | 1 | 98.80 | 0.23 | 0.43 |
| | 3 | 99.00 | 0.33 | 0.54 |
| | 6 | 99.95 | 0.39 | 0.66 |
| | 9 | 98.05 | 0.46 | 0.73 |
| | 9 (Aluminum tube) | 97.25 | 0.45 | 0.88 |
| | 12 | 98.36 | 0.39 | 0.60 |
| | 12 (Aluminum tube) | 98.7 | 0.36 | 0.56 |
| 30° C./ 65% RH | 0 | 98.48 | 0.14 | 0.30 |
| | 1 | Not tested | | |
| | 3 | Not tested | | |

TABLE 3-continued

Batch 3663-46 (1% minocycline gel) - ICH stability and compatibility studies

| Condition | Time (Months) | Minocycline % Label Claim | 4-Epi-minocycline Area % | Total Impurities (including 4-epi) |
|---|---|---|---|---|
| | 6 | 97.65 | 0.51 | 1.30 |
| | 12 | 98.75 | 0.52 | 0.77 |
| | 12 (Aluminum tube) | 97.90 | 0.38 | 0.61 |
| 40° C./ 75% RH | 0 | 98.48 | 0.14 | 0.30 |
| | 1 | 98.55 | 0.26 | 0.48 |
| | 3 | 98.70 | 0.34 | 0.58 |
| | 6 | 93.75 | 1.40 | 2.70 |
| | 6 (Aluminum tube) | 97.15 | 0.42 | 0.73 |

Samples were stored in laminate tubes, unless specified.

Therefore, in one aspect of the invention, a minocycline suspension formulation when stored at 40° C./75% RH for one month results in less than 0.3% of 4-epi-minocycline. In another aspect of the invention, a minocycline suspension formulation when stored at 40° C./75% RH for one month results in less than 0.26% of 4-epi-minocycline. In another aspect of the invention a minocycline suspension formulation when stored at 40° C./75% RH for three months results in less than 0.4% of 4-epi-minocycline. In another aspect of the invention, a minocycline suspension formulation when stored at 40° C./75% RH for three months results in less than 0.34% of 4-epi-minocycline. In another aspect of the invention a minocycline suspension formulation when stored at 40° C./75% RH for six months results in less than 2% of 4-epi-minocycline. In another aspect of the invention, a minocycline suspension formulation when stored at 40° C./75% RH for six months results in less than 1.4% of 4-epi-minocycline.

It should be understood that the measure of the 4-epi-minocycline is based on the amount of minocycline initially present. Therefore, if the amount of 4-epi-minocycline is measured to be 0.5%, that value is with respect to the starting amount of minocycline.

The impurity data that is reported above is based on a small batch size. In the experience of the inventors, it is expected that the level of 4-epi-minocycline will be increased in larger batches. For example, the initial levels of 0.14% of the 4-epiminocycline impurity listed above will likely be higher in large batches, such as those on a commercial scale. Because the Pharmacopeial requirements for 4-epi-minocycline are less than 6%, the amount of 4-epi-minocycline in the formulations described herein must be less than 6%.

The data above shows that the rate of formation of 4-epiminocycline appears to occur more rapidly initially than later. Without wishing to be bound by any particular theory other than the above observations, it is the belief of the inventors that the rate of formation of the 4-epiminocycline occurs more rapidly initially than later due to the solubility of the minocycline in the suspension.

As evident from the stability data above, the topical suspension minocycline formulations have an approximately 300% increase in the 4-epi-minocycline impurity after six months to one year storage at 25° C./60% RH and 30° C./65% RH. When stored at 40° C./75% RH for 1-3 months the formulation has an approximately 100% increase in, or doubling of the amount of, the 4-epi minocycline impurity.

The impurity data that is reported above is based on a small batch size. In the experience of the inventors, it is expected that the level of 4-epi-minocycline will be increased in larger batches. The Pharmacopeial requirements for 4-epi-minocycline are less than 6% which is believed to be a suitable maximum value for the presence of 4-epi-minocycline in the topical suspension of minocycline, although any value of between about 3% to about 6% is a suitable specification for the maximum level of 4-epi-minocycline.

Viscosity Studies

Some of the batches described above for stability also were periodically analyzed for viscosity. These values are provided below. These values are suitable for a topically applied formulation but it should be understood that a wider range of viscosity values are acceptable for this product. Viscosity can be controlled at least by the gelling polymers used in the formulation. As explained above, Versagel M750 was used to make example formulations but the other grades of Versagel M (e.g., 200, 500, 1600) can also be used. Further different brands of gelling polymers are expected to give suitable and similar results. As such, the formulations herein should not be considered as limited to a particular brand or type of gelling polymer.

TABLE 4

Batch 3663-46 (1% minocycline gel) - viscosity studies

| Condition | Time (Months) | Viscosity (cPs) |
|---|---|---|
| 25° C./60% RH | 0 | 11920 |
| | 1 | |
| | 3 | |
| | 6 | 11460 |
| | 9 | |
| | 12 | 10700 |
| 40° C./75% RH | 0 | 11920 |
| | 1 | |
| | 3 | |
| | 6 | 10760 |

Permeation Studies

Minocycline suspension formulation from Example 1 above was evaluated ex vivo for skin permeation (Franz cell and human skin). Minocycline suspension formulation as described in Example 1 (20 µL, 1% suspension gel) was applied to 2 cm$^2$ skin surface and permeation studied over a period of 48 hours. The results showed that there was approximately five times more minocycline present in epidermis and dermis as compared with the receptor chamber (approximately 530 ng in epidermis and dermis versus approximately 100 ng in receptor chamber)—this suggests that minocycline formulation as described in Example 1, on topical administration, will potentially result in lower systemic exposure and comparatively higher (than systemic) concentrations in epidermis, and dermis. In this ex vivo permeation study, majority of minocycline was unabsorbed and determined in the surface wash (Table 5).

TABLE 5

Distribution Across Skin Donors
Distribution of Minocycline and appearance of 4-Epi
minocycline in ex vivo Human Torso Skin
Over 48 hours from a Single Application of 1% Minocycline Gel.
Mean ± SE, n = 3 Donors, as Percent of Applied
Dose and Total Mass (µg/2-cm$^2$)

| Parameter | Minocycline |
|---|---|
| Mass Recovered | |
| Receptor (µg) | 0.096 ± 0.021 |
| Dermis (µg) | 0.023 ± 0.003 |
| Epidermis (µg) | 0.505 ± 0.037 |
| Stratum Corneum (µg) | 0.024 ± 0.001 |
| Surface Cleanse (µg) | 165.36 ± 1.64 |
| Percent Dose | |
| Receptor (%) | 0.05 ± 0.01 |
| Dermis (%) | 0.01 ± 0.00 |
| Epidermis (%) | 0.25 ± 0.02 |
| Stratum Corneum (%) | 0.01 ± 0.00 |
| Surface Cleanse (%) | 82.68 ± 0.82 |
| Total Recovery (%) | 83.00 ± 0.82 |

While several particular forms of the invention have been illustrated and described, it will be apparent that various modifications and combinations of the invention detailed in the text can be made without departing from the scope of the invention. For example, references to specific utilities or applications are not intended to be limiting in any manner and other utilities and applications could be substituted and remain within the scope of the invention. Accordingly, it is not intended that the invention be limited, except as by the appended claims.

The invention claimed is:

1. A topical suspension formulation comprising:
a tetracycline, or a pharmaceutically acceptable salt, hydrate, or polymorph thereof in a suspended form within the formulation;
a liquid medium which dissolves less than 5% of the active ingredient from the class of tetracyclines determined by HPLC at room temperature after 2 hours and comprises mineral oil; and
a polymeric hydrocarbon gelling agent,
wherein the tetracycline has a D90 particle size that has a value that is from about 4 microns to about 10 microns.

2. The topical suspension formulation of claim 1, wherein the tetracycline has a D90 particle size that has a value that is from about 4 microns to about 10 microns and a D50 particle size that has a value that is from about 1 micron to about 5 microns.

3. The topical suspension formulation of claim 1, wherein the tetracycline has a D90 particle size that has a value that is from about 4 microns to about 10 microns, a D50 particle size that has a value that is from about 1 micron to about 5 microns, and a D10 particle size that has a value that is from about 0.5 microns to about 1.5 microns.

4. The topical suspension formulation of claim 1 wherein the tetracycline is minocycline or doxycycline, or a pharmaceutically acceptable salt, hydrates or polymorph thereof.

5. The topical suspension formulation according to claim 4 wherein the concentration of minocycline is from about 0.05% to about 10%.

6. The topical suspension formulation of claim 5 wherein the concentration of 4-epi minocycline is not more than 4% after storage for 6 months at real-time (25° C./60% relative humidity (RH)) and at accelerated (40° C./75% RH) stability conditions, as determined by HPLC analysis.

7. The topical suspension formulation of claim 5 wherein the concentration of 4-epi minocycline in the minocycline suspension formulation when stored at 40° C./75% RH for one month results in less than 3% of 4-epi-minocycline, as determined by HPLC analysis.

8. The topical suspension formulation of claim 5 wherein the concentration of 4-epi minocycline in the minocycline suspension formulation when stored at 40° C./75% RH for three months results in less than 4% of 4-epi-minocycline, as determined by HPLC analysis.

9. The topical suspension formulation of claim 5 wherein the concentration of 4-epi minocycline is no more than 4% after storage for 12 months at real-time (25° C./60% RH) stability conditions, as determined by HPLC analysis.

10. The topical suspension formulation of claim 1, wherein the liquid medium is a non-comedogenic liquid medium.

11. The topical suspension formulation of claim 10, wherein the non-comedogenic liquid medium further comprises one or more of a light mineral oil, a minimally comedogenic oil and an additional non-comedogenic oil.

12. The topical suspension formulation of claim 1, wherein the liquid medium consists of mineral oil.

13. The topical suspension formulation of claim 10, wherein the non-comedogenic liquid medium is characterized as (a) resulting in less than 5% of the tetracycline active ingredient being dissolved in the medium at room temperature after 2 hours, as measured by HPLC and/or (b) resulting in less than 4% of 4-epi-minocycline, if minocycline is used as the active ingredient, when stored for 1 month at room temperature, as measured by HPLC.

14. The topical suspension formulation of claim 1, wherein the mineral oil constitutes at least about 70% of the suspension formulation.

15. The topical suspension formulation of claim 1, wherein the polymeric hydrocarbon gelling agent is a mixture of a mineral oil and one or more copolymers based on one or more monomers selected from $C_1$-$C_{10}$, or $C_1$ to $C_6$, or $C_2$ to $C_4$ alkene monomers, and $C_1$-$C_{10}$, or $C_1$ to $C_6$, or $C_2$ to $C_4$ phenylalkene monomers, or is a gel comprising an oil and one or more gelling polymers.

16. The topical suspension formulation of claim 15 wherein the one or more copolymers comprises an ethylene/propylene/styrene copolymer.

17. The topical suspension formulation of claim 15 wherein the one or more copolymers comprises a butylene/ethylene/styrene copolymer.

18. The topical suspension formulation of claim 15 wherein the suspension further comprises an anti-oxidant.

19. The topical suspension formulation of claim 15 wherein the polymeric gelling agent comprises ethylene/propylene/styrene copolymer and butylene/ethylene/styrene copolymer and butylated hydroxytoluene as an optional anti-oxidant.

20. The topical suspension formulation of claim 1, wherein the formulation is free of a skin penetration enhancing agent or an excipient that functions primarily or solely as a skin penetration enhancer.

21. The topical suspension formulation of claim 1 wherein the formulation is free of a compound that results in dissolution of the tetracycline active ingredient.

22. The topical suspension formulation of claim 21, wherein the compound that results in dissolution of the tetracycline active ingredient comprises one or more of water, hydrophilic solvents and emollient esters.

23. The topical suspension formulation of claim 1, wherein the liquid medium comprises a mixture of a non-comedogenic medium and a comedogenic medium and the non-comedogenic medium is present in a greater amount than the comedogenic medium.

24. The topical suspension formulation of claim 1, wherein the composition consists essentially of the pharmaceutically effective amount of minocycline, a non-comedogenic liquid medium that does not dissolve or minimally dissolves tetracycline, and the polymeric hydrocarbon gelling agent to thicken the composition and optionally one or more of 4-epi minocycline, colorants, dyes, fragrances and a sunscreen material.

25. The topical suspension formulation of claim 1, wherein the composition consists of the pharmaceutically effective amount of minocycline, a non-comedogenic liquid medium that does not dissolve or minimally dissolves tetracycline, and the polymeric hydrocarbon gelling agent to thicken the composition.

26. The topical suspension formulation of claim 1, wherein the composition consists of a pharmaceutically effective amount of minocycline, a non-comedogenic liquid medium that does not dissolve or minimally dissolves tetracycline, and a gelling agent to thicken the composition and 4-epi minocycline, and optionally one or more of a comedogenic liquid medium present at an amount less than the non-comedogenic liquid medium, colorants, dyes, fragrances and sunscreen materials.

27. The topical suspension formulation of claim 1, wherein the composition is nonfoamable and is free of a foaming adjuvant.

28. A method of treating an infection or inflammation of the skin, the method comprising topically administering to a subject in need of such treatment the suspension formulation of claim 1.

29. The method of treating an infection or inflammation of the skin of claim 28 wherein the disease is characterized as acne or rosacea.

30. A method of treating an ophthalmic disease or condition, the method comprising topically administering to a surface of the eye of a subject in need of such treatment a suspension formulation of claim 1.

31. The topical suspension formulation of claim 4, wherein the minocycline is crystalline minocycline free base.

32. The topical suspension formulation of claim 1, further comprising one or more of a sunscreen agent, a fragrance and a colorant or dye.

33. The topical suspension formulation of claim 1, further comprising a pharmaceutically effective amount of a retinoid selected from tretinoin, adapalene and tazarotene.

34. A topical minocycline suspension formulation for treating an individual afflicted with acne vulgaris, the composition consisting essentially of a pharmaceutically effective amount of minocycline, a hydrophobic liquid medium that does not dissolve or minimally dissolves tetracycline and comprises mineral oil, and a polymeric hydrocarbon gelling agent to thicken the composition, wherein:
the hydrophobic liquid medium is characterized as (a) resulting in less than 5% of the tetracycline active ingredient being dissolved in the medium at room temperature after 2 hours as determined by HPLC, and/or (b) results in less than 4% of 4-epi-minocycline (when minocycline is used as the active ingredient) when stored for 1 month at room temperature, as determined by HPLC.

35. The topical suspension formulation of claim 1, wherein the tetracycline has a D90 particle size that has a value that is one of about 4 microns, about 5 microns, about 6 microns, about 7 microns, about 8 microns, or about 9 microns, or a fractional value in between any of these values.

* * * * *